(12) United States Patent
Noel et al.

(10) Patent No.: US 8,263,666 B2
(45) Date of Patent: Sep. 11, 2012

(54) COMPOSITION IN THE FORM OF AN OIL-IN-WATER EMULSION AND USES THEREOF

(75) Inventors: Christine Noel, Fresnes (FR); Anne-France Livernette, Paris (FR)

(73) Assignee: L'Oreal, Paris (FR)

( * ) Notice: Subject to any disclaimer, the term of this patent is extended or adjusted under 35 U.S.C. 154(b) by 444 days.

(21) Appl. No.: 10/685,505

(22) Filed: Oct. 16, 2003

(65) Prior Publication Data

US 2004/0166128 A1 Aug. 26, 2004

Related U.S. Application Data

(60) Provisional application No. 60/427,931, filed on Nov. 21, 2002, provisional application No. 60/427,928, filed on Nov. 21, 2002.

(30) Foreign Application Priority Data

Oct. 29, 2002 (FR) ...................................... 02 13520
Oct. 29, 2002 (FR) ...................................... 02 13521

(51) Int. Cl.
*A61K 8/06* (2006.01)
*A61K 8/25* (2006.01)
*A61K 8/41* (2006.01)

(52) U.S. Cl. ........ 514/844; 514/848; 514/937; 514/938; 424/401; 424/59; 424/70.1; 424/78.02; 424/78.07; 424/78.08

(58) Field of Classification Search .................. 424/400, 424/401, 59, 70.1, 78.07, 78.02, 78.08; 514/848, 514/937, 938, 844

See application file for complete search history.

(56) References Cited

U.S. PATENT DOCUMENTS

| | | | |
|---|---|---|---|
| 5,192,747 A * | 3/1993 | Krstenansky | 514/15 |
| 5,874,086 A * | 2/1999 | Krstenansky et al. | 424/198.1 |
| 6,197,287 B1 * | 3/2001 | Mallo et al. | 424/70.16 |
| 6,241,976 B1 | 6/2001 | Esser et al. | |
| 6,296,859 B1 * | 10/2001 | Stoltz | 424/401 |
| 6,346,255 B1 * | 2/2002 | Fotinos | 424/401 |
| 6,465,402 B1 * | 10/2002 | Lorant | 510/136 |
| 6,653,280 B2 * | 11/2003 | Liang et al. | 514/2 |
| 6,998,426 B2 | 2/2006 | L'Alloret et al. | |
| 2001/0002257 A1 * | 5/2001 | Stolz | 424/401 |
| 2003/0141260 A1 * | 7/2003 | Corbin et al. | 210/748 |
| 2004/0067213 A1 | 4/2004 | Schmid et al. | |

FOREIGN PATENT DOCUMENTS

| | | |
|---|---|---|
| DE | 101 02 009 | 8/2002 |
| EP | 1055406 * | 11/2000 |
| FR | 2 771 633 | 6/1999 |
| FR | 2771632 * | 6/1999 |
| WO | WO93/05762 * | 4/1993 |
| WO | WO 98/09611 | 3/1998 |
| WO | WO 98/35649 | 8/1998 |
| WO | WO 02/03952 | 1/2002 |
| WO | WO0203952 * | 1/2002 |

* cited by examiner

*Primary Examiner* — Gina C Yu

(74) *Attorney, Agent, or Firm* — Oblon, Spivak, McClelland, Maier & Neustadt, L.L.P.

(57) ABSTRACT

Composition for topical application in the form of an oil-in-water emulsion containing an oily phase dispersed in an aqueous phase, and a hydrophilic polymer, the composition further containing (1) at least one elastomeric organopolysiloxane and (2) at least one lipophilic compound chosen from lipophilic amino acid compounds and lipophilic salicylic acid compounds. Uses thereof, including topical application to the skin, lips, hair, etc. Stabilization of certain emulsions using a lipophilic compound.

17 Claims, No Drawings

COMPOSITION IN THE FORM OF AN OIL-IN-WATER EMULSION AND USES THEREOF

REFERENCE TO PRIOR APPLICATIONS

This application claims priority to U.S. provisional applications 60/427931 filed Nov. 21, 2002, and 60/427,928 filed Nov. 21, 2002, and to French patent applications 0213520 filed Oct. 29, 2002, and 0213521 filed Oct. 29, 2002, all incorporated herein by reference.

FIELD OF THE INVENTION

The present invention relates to a composition in the form of an oil-in-water emulsion comprising an oily phase dispersed in an aqueous phase, and a hydrophilic polymer. Preferably the composition is suitable for topical application, and preferably contains (1) at least one elastomeric organopolysiloxane and (2) at least one lipophilic derivative (compound) preferably chosen from lipophilic salicylic acid derivatives (compounds) and lipophilic amino acid derivatives (compounds). While not bound by any theory whatever, it is believed that the lipophilic compound makes it possible to obtain a composition that is stable even in the presence of high amounts of elastomeric organopolysiloxane.

The composition of the invention has the advantage of being stable and gentle on application. It may especially constitute a cosmetic composition.

The invention also relates to the use of the composition according to the invention, especially to combat the signs of ageing of the skin and/or to improve the radiance of the complexion of the skin.

The invention also relates to the use of the composition according to the invention, and especially to the use of the salicylic acid compound(s) and/or of the amino acid compound(s), to stabilize an oil-in-water emulsion containing a hydrophilic polymer and an elastomeric organopolysiloxane.

Additional advantages and other features of the present invention will be set forth in part in the description that follows and in part will become apparent to those having ordinary skill in the art upon examination of the following or may be learned from the practice of the present invention. The advantages of the present invention may be realized and obtained as particularly pointed out in the appended claims. As will be realized, the present invention is capable of other and different embodiments, and its several details are capable of modifications in various obvious respects, all without departing from the present invention. The description is to be regarded as illustrative in nature, and not as restrictive.

BACKGROUND OF THE INVENTION

For various reasons associated in particular with better comfort during their use (softness, emollience and the like), current cosmetic compositions are usually in the form of an emulsion of the oil-in-water (O/W) type consisting of an aqueous dispersing continuous phase and an oily dispersed discontinuous phase, or of an emulsion of the water-in-oil (W/O) type consisting of an oily dispersing continuous phase and an aqueous dispersed discontinuous phase. O/W emulsions are the ones most sought in the cosmetics field, since they comprise an aqueous phase as external phase, which gives them a fresher, less greasy and lighter feel than W/O emulsions when they are applied to the skin.

The emulsions are generally stabilized with suitable emulsifying surfactants, which, by virtue of their amphiphilic structure, become positioned at the oil/water interface and thus stabilize the dispersed droplets. However, these emulsifiers have the drawback of being penetrating and potentially irritant to the skin, eyes and the scalp, especially in the case of individuals with sensitive skin.

In addition, such emulsions may have insufficient cosmetic and physicochemical properties (oily feel, instability over time). Increasing the surfactant content generally does not solve the problems mentioned. The required stability is not always achieved and the cosmetic properties are not improved (waxy, heavy feel, lack of freshness on application). Moreover, as mentioned above, it is also not recommended to use an excessively high content of surfactant for reasons of harmfulness.

One solution for overcoming the instability of O/W emulsions (creaming and phase separation) consists in introducing into the emulsion thickeners whose function is to create, in the aqueous phase, a gelled matrix that serves to set the oily droplets and ensures mechanical maintenance of the whole emulsion. Moreover, it has been envisaged to replace the surfactants with hydrophilic polymers comprising in their chain a hydrophilic portion and a hydrophobic portion, such as copolymers of $C_{10}$-$C_{30}$-alkyl acrylate and of acrylic or methacrylic acid, for instance the product "Pemulen TR2" sold by the company Goodrich, or with hydrophilic polymers derived from 2-acrylamido-2-methylpropanesulphonic acid (AMPS), as described in document EP-A-815 844.

However, emulsions stabilized with hydrophilic polymers may have a coarse feel. To improve the softness of these emulsions, the Asssignee has sought to incorporate therein compounds that afford softness, and especially elastomeric organopolysiloxanes (also known as silicone elastomers), such as the products sold by Shin-Etsu under the name KSG. However, the Assignee has found that when these elastomeric organopolysiloxanes are introduced in large amount, and especially in an amount of greater than 1% (of active material); they have a tendency to destabilize the emulsion containing the hydrophilic polymer.

One object of the invention is the provision of oil-in-water (O/W) emulsions that show good cosmetic properties (softness), which are stable, i.e. which do not undergo a phase separation and do not release oil, irrespective of the amount of silicone elastomer contained in the emulsion.

DETAILED DESCRIPTION OF THE PREFERRED EMBODIMENTS

The inventors have discovered, unexpectedly, that the use of a lipophilic salicylic acid derivative or of a lipophilic amino acid derivative, or both, makes it possible to produce oil-in-water emulsions containing both a hydrophilic polymer and a silicone elastomer, which are stable, this stability persisting even when the content of silicone elastomer is high. In addition, depending on the polymer used and in particular when the hydrophilic polymer is an AMPS polymer, emulsions that are stable even though they may be free of surfactant conventionally used in this type of emulsion may be prepared.

Thus, the present invention relates to a composition in the form of an oil-in-water emulsion comprising an oily phase dispersed in an aqueous phase, and a hydrophilic polymer, characterized in that it contains (1) at least one elastomeric organopolysiloxane and (2) a lipophilic derivative chosen from lipophilic amino acid derivatives, including salts, and lipophilic salicylic acid derivatives of formula (I) below or a salt of such a derivative:

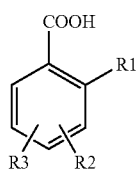

(I)

in which:

$R_1$ represents a hydroxyl radical or an ester of formula:

—O—CO—$R_4$ in which $R_4$ is a saturated or unsaturated aliphatic radical containing from 1 to 26 carbon atoms and preferably from 1 to 18 carbon atoms, an amine or thiol function optionally substituted with an alkyl radical containing from 1 to 18 carbon atoms and preferably from 1 to 12 carbon atoms, $R_2$ and $R_3$, independently of each other, are in position 3, 4, 5 or 6 on the benzene ring and represent, independently of each other, a hydrogen atom or a radical:

—(O)$_n$—(CO)$_m$—$R_5$ in which n and m, independently of each other, are each an integer equal to 0 or 1; on condition that $R_2$ and $R_3$ are not simultaneously hydrogen atoms;

$R_5$ represents a hydrogen, a linear, branched or cyclized saturated aliphatic radical containing from 1 to 18 carbon atoms, an unsaturated radical containing from 3 to 18 carbon atoms, bearing one to nine conjugated or non-conjugated double bonds, the radicals optionally being substituted with at least one substituent chosen from halogen atoms (fluorine, chlorine, bromine or iodine), trifluoromethyl radicals, hydroxyl in free form or esterified with an acid containing from 1 to 6 carbon atoms, or carboxyl in free form or esterified with a lower alcohol containing from 1 to 6 carbon atoms, or an aromatic radical containing from 6 to 10 carbon atoms.

While not bound by any theory of operation whatever, it is believed that the lipophilic derivative used in the composition according to the invention makes it possible to obtain a stable emulsion. A subject of the invention is thus also the use of a lipophilic derivative chosen from lipophilic salicylic acid derivatives of formula (I) and lipophilic amino acid derivatives, to stabilize an oil-in-water emulsion containing an elastomeric organopolysiloxane and a hydrophilic polymer.

Since the compositions of the invention have a preferred use in the area of topical application, it preferably contains a physiologically acceptable medium. The expression "physiologically acceptable medium" means a non-toxic medium that may be applied to human skin (including the interior of the eyelids), lips, nails or hair.

Lipophilic Salicylic Acid Derivatives

The lipophilic salicylic acid derivative(s) preferably used in the composition of the invention are compounds of formula (I) above.

Highly preferred salicylic acid derivative of formula (I) include those where $R_1$ represents a hydroxyl radical, $R_2$ represents a hydrogen atom, $R_3$ is in position 5 of the benzene nucleus and $R_5$ represents a saturated aliphatic radical containing from 3 to 15 carbon atoms.

According to one preferred embodiment of the invention, the salicylic acid derivative of formula (I) is chosen from 5-n-octanoylsalicylic acid, 5-n-deca-noylsalicylic acid, 5-n-dodecanoylsalicylic acid, 5-n-octylsalicylic acid, 5-n-hepty-loxysalicylic acid, 4-n-heptyloxysalicylic acid, 5-tert-octylsalicylic acid, 3-tert-butyl-5-methylsalicylic acid, 3-tert-butyl-6-methylsalicylic acid, 3,5-diisopropylsalicylic acid, 5-butoxysalicylic acid, 5-octyloxysalicylic acid, 5-propanoylsalicylic acid, 5-n-hexadecanoylsalicylic acid, 5-n-oleoylsalicylic acid, 5-benzoylsalicylic acid, monovalent and divalent salts thereof, and mixtures thereof. It is more particularly 5-n-octanoylsalicylic acid (INCI name: Capryloyl salicylic Acid).

Lipophilic Amino Acid Derivative

The lipophilic amino acid derivative(s) used in the composition of the invention is preferably a glycine derivative, more particularly a compound of formula (II) below or a salt of such a compound:

(II)

in which R is chosen from alkyl (i.e. saturated) and alkenyl (i.e. unsaturated) radicals containing from 6 to 22 carbon atoms and preferably from 7 to 18 carbon atoms, and R' is chosen from hydrogen and alkyl radicals containing from 1 to 30 carbon atoms and preferably from 1 to 10 carbon atoms. R' is preferably hydrogen.

Highly preferred compounds of formula (II) include capryloylglycine, which is a compound of formula (II) in which R is $CH_3(CH_2)_6$ and R'=H; undecylenoylglycine, which is a compound of formula (II) in which R is $CH_2$=$CH(CH_2)_8$ and R'=H; and mixtures thereof.

These compounds may be used in unmodified form or in mixtures containing them. According to one preferred embodiment of the invention, the capryloylglycine is used in the form of the mixture sold by the company SEPPIC under the name Sepicontrol A5, comprising 25% capryloylglycine, 3% cinnamon extract and 7% sarcosine in a mixture of water (45%) and hexylene glycol (20%).

One or more lipophilic salicylic acid and/or amino acid derivatives may be used. The amount of lipophilic derivative (s) may range, for example, from 0.01% to 20%, preferably from 0.05% to 10% and better still from 0.1% to 5% by weight relative to the total weight of the composition.

Elastomeric Organopolysiloxane

The composition of the invention comprises at least one elastomeric organopolysiloxane, which is preferably at least partially crosslinked. The term "elastomeric" means a solid, soft, deformable material with viscoelastic properties especially having the consistency of a sponge or a soft sphere. Its modulus of elasticity is such that this material withstands deformation and has limited stretchability and contractability. This material is capable of regaining its original shape after stretching. This elastomer is formed from polymer chains of high molecular weight, the mobility of which is limited by a uniform network of crosslinking points.

The elastomeric organopolysiloxanes used in the composition according to the invention are preferably partially or totally crosslinked. They are preferably in the form of particles. In a particular embodiment the elastomeric organopolysiloxane particles range from 0.1 to 500 μm, preferably from 3 to 200 µm and better still from 3 to 50 µm in size. These particles may have any shape, for example they may be spherical, flat or amorphous.

When they are included in an oily phase, these elastomeric organopolysiloxanes become transformed, depending on the content of oily phase used, into a product of spongy appearance when they are used in the presence of small amounts of oily phase, or into a homogeneous gel in the presence of larger amounts of oily phase. The gelation of the oily phase with these elastomers may be total or partial.

Thus, the elastomers of the invention may be conveyed in the form of an anhydrous gel consisting of an elastomeric organopolysiloxane and of an oily phase. The oily phase used in the manufacture of the anhydrous gel of elastomeric organopolysiloxane may comprise one or more oils that are liquid at room temperature (25° C.) and especially those chosen from hydrocarbon-based oils and/or silicone oils. Advantageously, the oily phase is a silicone liquid phase, containing one or more oils chosen from polydimethylsiloxanes containing a linear or cyclic chain, which are liquid at room temperature, optionally comprising an alkyl or aryl chain that is pendent or at the end of the chain, the alkyl chain containing from 1 to 6 carbon atoms.

The elastomeric organopolysiloxanes used according to the invention may be chosen from the crosslinked polymers described in patent application EP-A-0 295 886 and from those described in patent U.S. Pat. No. 5,266,321.

They are preferably elastomeric organopolysiloxanes obtained by addition and crosslinking reaction, in the presence of a catalyst, preferably a catalyst of the platinum type, of at least:
  (a) one organopolysiloxane containing two vinyl groups in α-ω position on the silicone chain per molecule; and
  (b) one organopolysiloxane containing at least two hydrogen atoms linked to a silicon atom per molecule.

The first organopolysiloxane (i) is chosen from polydimethylsiloxanes; it is preferably an α,ω-dimethylvinylpolydimethylsiloxane.

The organopolysiloxane is preferably in a gel obtained according to the following steps:
  (a) mixing of the first and second organopolysiloxanes (i) and (ii);
  (b) adding an oily phase to the mixture from step (a);
  (c) polymerizing the first and second organopolysiloxanes (i) and (ii) in the oily phase in the presence of a catalyst, preferably a platinum catalyst.

The elastomeric organopolysiloxanes used in the composition of the invention may be, for example, those sold under the names: KSG 6 by the company Shin-Etsu; Trefil E-505C or Trefil E-506C by the company Dow Corning; Gransil (SR-CYC, SR DMF10, SR-DC556) by the company Grant Industries, or those sold in the form of ready-made gels: KSG 15, KSG 16, KSG 17, KSG 18, KSG 26A or KSG 26B from the company Shin-Etsu; Gransil SR 5CYC gel, Gransil SR DMF 10 gel and Gransil SR DC556 gel from the company Grant Industries; 1229-02-167 and 1229-02-168 from the company General Electric. A mixture of silicone elastomers, and especially a mixture of these commercial products, may also be used.

The elastomeric organopolysiloxane used in the composition of the invention is preferably in the form of an anhydrous gel, and especially of an anhydrous gel formed from non-spherical particles of elastomeric organopolysiloxane, such as the KSG products. The elastomeric organopolysiloxane is preferably introduced into the oily phase of the emulsion according to the invention.

The elastomeric organopolysiloxane(s) used according to the invention are present in an amount of active material that varies depending on the desired aim. This amount may range, for example, from 0.5% to 20%, preferably from 1% to 15% and better still from 5% to 10% relative to the total weight of the composition.

Hydrophilic Polymers

Hydrophilic polymers are water-soluble or water-dispersible polymers. The expression "water-soluble or water-dispersible polymer" means a polymer which, when introduced into water to a concentration equal to 1%, gives a macroscopically homogeneous solution whose light transmittance, at a wavelength equal to 500 nm, through a sample 1 cm thick, is at least 10%.

These polymers are gelling agents, and they may be chosen in particular from carboxyvinyl polymers; acrylic or methacrylic copolymers; natural gums; polysaccharides; acrylamide polymers (homopolymers and copolymers); and mixtures thereof. These polymers may be in unmodified form or in the form of a latex (as dispersions).

Examples of carboxyvinyl polymers that may be mentioned include crosslinked acrylic acid polymers (INCI name: Carbomer), such as the products sold under the names Carbopol 980, 981, 954, 2984 and 5984 by the company Noveon or the products sold under the names Synthalen M and Synthalen K by the company 3 VSA.

Acrylic or methacrylic copolymers that may especially be mentioned include copolymers of $C_{10}$-$C_{30}$ alkyl acrylates and of acrylic or methacrylic acid or of an ester thereof, sold under the names Pemulen TR1, Pemulen TR2 and Carbopol 1342 by the company Noveon (INCI name: Acrylates/C10-30 Alkyl Acrylate Crosspolymer).

Examples of natural gums that may be mentioned include xanthan gum, gellan gum and carob gum.

Polysaccharides that may especially be mentioned include cellulose derivatives, for instance hydroxypropylmethylcellulose and carboxymethylcellulose.

Acrylamide polymers that may especially be mentioned include poly(meth)acrylamido($C_1$-$C_4$)alkylsulphonic acids. These polymers are preferably crosslinked and, in addition, they are preferably partially or totally neutralized.

Among these polymers that may especially be mentioned are:
  polyacrylamidomethanesulphonic acid,
  polyacrylamidoethanesulphonic acid,
  polyacrylamidopropanesulphonic acid,
  poly-2-acrylamido-2-methylpropanesulphonic acid,
  poly-2-methylacrylamido-2-methylpropanesulphonic acid,
  poly-2-acrylamido-n-butanesulphonic acid.

Polymers of this type and especially crosslinked and partially or totally neutralized poly-2-acrylamido-2-methylpropanesulphonic acids are known, described and prepared in document DE-A-196 25 810.

The preferred poly(meth) acrylamido ($C_1$-$C_4$)-alkylsulphonic acids are crosslinked and at least 90% neutralized. These polymers may be crosslinked especially with a crosslinking unit containing at least two olefinic double bonds. The crosslinking units containing at least two olefinic double bonds may be chosen, for example, from dipropylene glycol diallyl ether, polyglycol diallyl ethers, triethylene glycol divinyl ether, hydroquinone diallyl ether, tetraallyloxyethane or other allyl or vinyl ethers of polyfunctional alcohols, tetraethylene glycol diacrylate, triallylamine, trimethylolpropane diallyl ether, methylenebisacrylamide and divinylbenzene.

The crosslinking units containing at least two olefinic double bonds are even more particularly chosen from those corresponding to general formula (III) below:

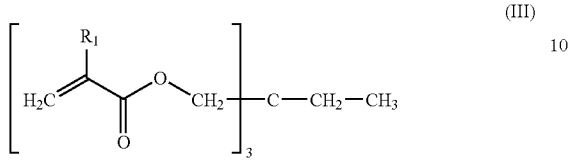

in which $R_1$ denotes a hydrogen atom or a $C_1$-$C_4$ alkyl radical. The crosslinking unit may more particularly be trimethylolpropane triacrylate ($R_1$=methyl)

The preferred poly(meth) acrylamido ($C_1$-$C_4$)-alkylsulphonic acids are especially poly-2-acrylamido-2-methylpropanesulphonic acids that are characterized in that they comprise, randomly distributed:

a) from 90% to 99.9% by weight of units of formula (IV) below:

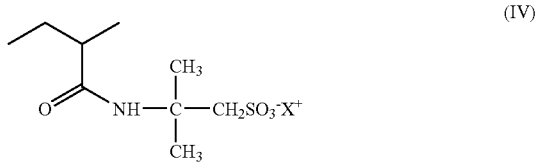

in which $X^+$ denotes a cation or a mixture of cations, including $H^+$, b) from 0.01% to 10% by weight of at least one crosslinking unit containing at least two olefinic double bonds, the weight proportions being defined relative to the total weight of the polymer.

$X^+$ represents a cation or a mixture of cations chosen in particular from a proton ($H^+$), an alkali metal cation, a cation equivalent to that of an alkaline-earth metal, or an ammonium ion.

The crosslinked and neutralized poly-2-acryl-amido-2-methylpropanesulphonic acid used preferably comprises from 98% to 99.5% by weight of units of formula (III) and from 0.5% to 2% by weight of crosslinking units, the crosslinking unit preferably being trimethylolpropane triacrylate.

The crosslinked and partially or totally neutralized poly-2-acrylamido-2-methylpropanesulphonic acids are generally known under the name "Ammonium Polyacrylamido-2-methylpropanesulphonate" or "Ammonium Polyacryldimethyltauramide" (INCI name).

A material that is particularly preferred according to the invention is the one sold by the company Clariant under the trade name Hostacerin AMPS, which is a crosslinked poly-2-acrylamido-2-methyl-propanesulphonic acid partially neutralized with ammonia.

The crosslinked poly(meth)acrylamido($C_1$-$C_4$)-alkylsulphonic acids may be obtained according to the known preparation process comprising the following steps:

(a) the 2-(meth)acrylamido($C_1$-$C_4$)alkylsulphonic acid monomer in free form is dispersed or dissolved in a solution of tert-butanol or in a solution of water and tert-butanol;

(b) the monomer solution or dispersion obtained in (a) is neutralized with one or more mineral or organic bases, preferably aqueous ammonia, in an amount producing a degree of neutralization of the sulphonic acid functions of the polymer ranging from 0 to 100%;

(c) the crosslinking monomer(s) is(are) added to the solution or dispersion obtained in (b);

(d) a standard free-radical polymerization is performed in the presence of free-radical initiators at a temperature ranging from 10 to 150° C., the polymer precipitating in the tert-butanol-based solution or dispersion.

Acrylamide polymers that may also be mentioned include the crosslinked copolymer of acrylamide and of 2-acrylamido-2-methylpropanesulphonic acid, in particular the mixture sold under the name Sepigel 305 by the company SEPPIC, which is in the form of an emulsion containing about 40% of copolymer (INCI name: polyacrylamide/C13-14 Isoparaffin/laureth-7).

The hydrophilic polymer used in the composition of the invention is preferably introduced into the aqueous phase of the emulsion according to the invention.

According to one preferred embodiment of the invention, the hydrophilic polymer is a crosslinked and partially or totally neutralized poly-2-acrylamido-2-methylpropanesulphonic acid, in particular the ammonium salt of such an acid.

The amount of hydrophilic polymer(s) active material preferably ranges from 0.1% to 10% by weight, preferentially from 0.2% to 5% by weight and better still from 0.5% to 2% by weight relative to the total weight of the composition.

Oily Phase

Besides the oils that may be present in the elastomeric organopolysiloxane gel, the oily phase may be of any nature and may comprise oils, waxes or gums that are solid at room temperature, pasty fatty substances of animal, plant, mineral or synthetic origin, and mixtures thereof.

As oils that may be used in the composition of the invention, mention may be made especially of:

hydrocarbon-based oils of animal origin, such as perhydrosqualene;

hydrocarbon-based oils of plant origin, such as liquid fatty acid triglycerides, for example sunflower oil, maize oil, soybean oil, marrow oil, coriander oil, grapeseed oil, sesame seed oil, hazelnut oil, apricot oil, macadamia oil, castor oil, avocado oil, caprylic/capric acid triglycerides such as those sold by the company Stearineries Dubois or those sold under the names Miglyol 810, 812 and 818 by the company Dynamit Nobel;

oils of formula $R^1COOR^2$ in which $R^1$ represents a higher fatty acid residue containing from 7 to 19 carbon atoms and $R^2$ represents a branched hydrocarbon-based chain containing from 3 to 20 carbon atoms, for instance purcellin oil, isopropyl myristate, and alcohol or polyalcohol octanoates, decanoates or ricinoleates;

linear or branched hydrocarbons of mineral or synthetic origin, such as volatile or non-volatile liquid paraffins and derivatives thereof, petroleum jelly, polydecenes, and hydrogenated polyisobutene such as Parleam® oil;

synthetic ethers of formula $R^3OR^4$ in which $R^3$ is a $C_3$ to $C_{19}$ alkyl radical and $R^4$ is a $C_3$ to $C_{20}$ alkyl radical;

fatty alcohols, for instance octyldodecanol or oleyl alcohol;

partially hydrocarbon-based fluoro oils and/or fluorosilicone oils, for instance perfluoropolyesters;

silicone oils such as polymethylsiloxanes containing a linear or cyclic silicone chain, which are liquid or pasty at room temperature, phenyldimethicones, phenyltrimethicones, polymethylphenylsiloxanes and alkylpolydimethylsiloxanes with a $C_2$ to $C_{20}$ alkyl chain; mixtures thereof.

According to one preferred embodiment of the invention, the oily phase comprises at least one volatile oil. The term "volatile oil" means in particular an oil capable of evaporating, in less than one hour, on contact with the skin or the lips, especially one having a non-zero vapour pressure ranging in particular from $10^{-3}$ to 300 mmHg (at room temperature and atmospheric pressure) and preferably greater than 0.3 mmHg. Volatile oils that may especially be mentioned include volatile silicone oils, such as polymethylsiloxanes with a linear or cyclic silicone chain, and especially cyclomethicone silicone oils, for instance cyclopentasiloxane, cyclohexasiloxane and cyclotetrasiloxane, and mixtures thereof.

The amount of oily phase in the composition of the invention may range from 1% to 50% by weight, preferably from 5% to 40% and better still from 10% to 30% by weight relative to the total weight of the composition.

Aqueous Phase

The amount of aqueous phase in the composition of the invention may preferably range from 50% to 99% by weight, preferably from 60% to 95% and better still from 70% to 90% by weight, relative to the total weight of the composition.

The aqueous phase comprises at least water. It may also comprise one or more water-soluble solvents. Examples of water-soluble solvents that may be mentioned include linear or branched monoalcohols containing from 1 to 8 carbon atoms, for instance ethanol, propanol, butanol, isopropanol and isobutanol; polyethylene glycols containing from 6 to 80 ethylene oxides; polyols, for instance propylene glycol, glycerol, isoprene glycol and butylene glycol.

According to one preferred embodiment of the invention, the emulsion of the invention is free of surfactant conventionally used in O/W emulsions and it consequently has the advantage of not being irritating to the skin, particularly sensitive skin. Surfactants, in particular irritating surfactants, thus may be excluded. In addition, this emulsion has the advantage of allowing the incorporation of heat-sensitive active agents, since it can be manufactured at room temperature.

Adjuvants

The compositions of the invention may contain adjuvants. Examples of adjuvants that may be mentioned include active agents, preserving agents, antioxidants, complexing agents, pH adjusters (acidic or basic), fragrances, bactericides, odour absorbers, fillers, dyestuffs (pigments or dyes) and lipid vesicles. These adjuvants can be used in their usual proportions in the cosmetics field, for example from 0.01% to 30% of the total weight of the emulsion, and, depending on their nature, they may be introduced into the aqueous phase and/or into the oily phase of the emulsion, or alternatively into vesicles. These adjuvants and the concentrations thereof should be such that they do not modify the property desired for the emulsion of the invention.

As active agents that may be used in the composition of the invention, examples that may be mentioned include enzymes (for example lactoperoxydase, lipase, protease, phospholipase or cellulases); flavonoids; moisturizers such as protein hydrolysates; sodium hyaluronate; polyols, for instance glycerol, glycols, for instance polyethylene glycols, and sugar derivatives; antiinflammatories; procyannidol oligomers; vitamins, for instance vitamin A (retinol), vitamin E (tocopherol), vitamin C (ascorbic acid), vitamin B5 (panthenol) and vitamin B3 (niacinamide), derivatives of these vitamins (especially esters) and mixtures thereof; urea; caffeine; depigmenting agents such as kojic acid, hydroquinone and caffeic acid; salicylic acid and its derivatives; α-hydroxy acids such as lactic acid and glycolic acid, and derivatives thereof; retinoids such as carotenoids and vitamin A derivatives; sunscreens; hydrocortisone; melatonin; extracts of algae, of fungi, of plants, of yeasts or of bacteria; steroids; antibacterial active agents, for instance 2,4,4'-trichloro-2'-hydroxydiphenyl ether (or Triclosan), 3,4,4'-trichlorocarbanilide (or Triclocarban); matting agents, for instance fibres; tensioning agents; ceramides; essential oils; and mixtures thereof; and any active agent that is suitable for the final aim of the composition.

Examples of steroids that may be mentioned include dehydroepiandrosterone (or DHEA), and also (1) its biological precursors and derivatives, in particular the salts and esters of DHEA, such as DHEA sulphate and salicylate, 7-hydroxy DHEA, 7-keto DHEA, esters of 7-hydroxy and 7-keto DHEA, especially 3-β-acetoxy-7-oxo DHEA, and (2) its chemical precursors and derivatives, in particular sapogenins such as diosgenin or hecogenin, and/or derivatives thereof such as hecogenin acetate, and/or natural extracts containing it, and especially Dioscorea extracts, such as wild yam.

The compositions in accordance with the invention may also comprise at least one organic photoprotective agent and/or at least one mineral photoprotective agent that is active in the UVA and/or UVB range (absorbers), which are water-soluble or liposoluble, or insoluble in the cosmetic solvents commonly used.

The organic photoprotective agents are preferably chosen especially from anthranilates; cinnamic derivatives; dibenzoylmethane derivatives; salicylic derivatives and camphor derivatives; triazine derivatives such as those described in documents U.S. Pat. No. 4,367,390, EP-A-863 145, EP-A-517 104, EP-A-570 838, EP-A-796 851, EP-A-775 698, EP-A-878 469, EP-A-933 376, EP-A-507 691, EP-A-507 692, EP-A-790 243 and EP-A-944624; benzophenone derivatives; β,β-diphenylacrylate derivatives; benzotriazole derivatives; benzalmalonate derivatives; benzimidazole derivatives; imidazolines; bis-benzazolyl derivatives as described in documents EP-A-669 323 and U.S. Pat. No. 2,463,264; p-aminobenzoic acid (PABA) derivatives; methylenebis (hydroxyphenylbenzotriazole) derivatives as described in documents U.S. Pat. No. 5,237,071, U.S. Pat. No. 5,166,355, GB-A-2 303 549, DE-A-197 26 184 and EP-A-893 119; screening polymers and screening silicones such as those described especially in document WO-A-93/04665; dimers derived from α-alkylstyrene, such as those described in document DE-A-198 55 649; 4,4-diaryl-butadienes as described in documents EP-A-967 200, DE-A-197 46 654, DE-A-197 55 649, EP-A-1 008 586, EP-A-1 133 980 and EP-A-133 981, and mixtures thereof.

The organic photoprotective agents that are more particularly preferred are chosen from the following compounds:
  ethylhexyl salicylate sold under the trade name Neo Heliopan OS by Haarmann & Reimer;
  ethylhexyl methoxycinnamate sold especially under the trade name Parsol MCX by Hoffmann LaRoche;
  octocrylene (2-ethylhexyl α-cyano-β,β-diphenyl-acrylate) sold especially under the trade name Uvinul N539 by BASF;
  phenylbenzimidazolesulphonic acid,
  Benzophenone-3 or Oxybenzone, sold under the trade name Uvinul M40 by BASF;

Benzophenone-4 sold under the trade name Uvinul MS40 by BASF;

4-methylbenzylidenecamphor sold under the trade name Eusolex 6300 by Merck;

terephthalylidenedicamphorsulphonic acid manufactured under the name Mexoryl SX by Chimex;

disodium phenyldibenzimidazoletetrasulphonate;

2,4,6-tris(diisobutyl 4'-aminobenzalmalonate)-s-triazine;

anisotriazine sold under the trade name Tinosorb S by Ciba Geigy;

butylmethoxydibenzoylmethane sold especially under the trade name Parsol 1789 by Hoffmann LaRoche;

and mixtures thereof.

Examples of mineral photoprotective agents (or physical sunblocks) that may be mentioned include coated or uncoated metal oxide pigments and nanopigments, especially titanium oxide, iron oxide, zirconium oxide, zinc oxide or cerium oxide, and mixtures thereof, these oxides possibly being in the form of optionally coated microparticles or nanoparticles (nanopigments).

Examples of fillers that may be mentioned include polyamide (Nylon) particles and especially those sold under the name Orgasol by the company Atochem; polyethylene powders; microspheres based on acrylic copolymers, such as those made of ethylene glycol dimethacrylate/lauryl methacrylate copolymer, sold by the company Dow Corning under the name Polytrap; polymethyl methacrylate microspheres, sold under the name Microsphere M-100 by the company Matsumoto or under the name Covabead LH85 by the company Wackherr; ethylene-acrylate copolymer powders, for instance those sold under the name Flobeads by the company Sumitomo Seika Chemicals; expanded powders such as hollow microspheres and especially microspheres formed from a terpolymer of vinylidene chloride, of acrylonitrile and of methacrylate and sold under the name Expancel by the company Kemanord Plast under the references 551 DE 12 (particle size of about 12 μm and density of 40 kg/m$^3$), 551 DE 20 (particle size of about 30 μm and a density of 65 kg/m$^3$) and 551 DE 50 (particle size of about 40 μm), or the microspheres sold under the name Micropearl F 80 ED by the company Matsumoto; powders of natural organic materials such as starch powders, especially of corn starch, wheat starch or rice starch, which may or may not be crosslinked, such as the starch powders crosslinked with octenylsuccinate anhydride, sold under the name Dry-Flo by the company National Starch; silicone resin microbeads such as those sold under the name Tospearl by the company Toshiba Silicone, especially Tospearl 240; silica; metal oxides such as titanium dioxide or zinc oxide; mica; fibres such as Nylon 6 (or polyamide 6) and Nylon 6,6 (or polyamide 66) fibres, and mixtures thereof. The amount of filler(s) may range, for example, from 0.05% to 20% by weight and better still 0.1% to 10% by weight relative to the total weight of the composition.

The composition of the invention is preferably used in topical application and it may in particular constitute a cosmetic or dermatological composition. This composition may be more or less fluid and may have the appearance of a white or coloured cream, an ointment, a milk, a lotion, a serum, a paste or a mousse. The composition of the invention may be applied topically to the human face, including around the eyes, the body and also the scalp.

The composition that is the subject of the invention finds application especially in a wide variety of cosmetic treatments of the skin, the lips and the hair, including the scalp, especially for treating, protecting, caring for, removing makeup from and/or cleansing the skin, the lips and/or the hair, and/or for making up the skin and/or the lips (with incorporation of pigments and/or dyes) and/or for antisun protection (with incorporation of photo-protective agents). It may be intended in particular for combating the signs of ageing of the skin, for instance an anti-ageing composition for the skin, and especially for improving the radiance of the complexion of the skin. It may be used in any other application, especially for the skin, that is suitable for the desired aim depending on the active agents present in the composition.

Thus, one subject of the invention is also the cosmetic use of the cosmetic composition as defined above for treating, protecting, caring for, removing makeup from and/or cleansing the skin, the lips and/or the hair, and/or for making up the skin and/or the lips.

Another subject of the invention is a cosmetic process for treating the skin, including the scalp, the hair and/or the lips, characterized in that a cosmetic composition as defined above is applied to the skin, the hair and/or the lips.

Another subject of the invention is the cosmetic use of a cosmetic composition as defined above to combat the signs of ageing of the skin and/or to improve the radiance of the complexion of the skin.

The examples that follow will enable the invention to be understood more clearly, without, however, being limiting in nature. The amounts indicated are weight percentages, unless otherwise mentioned.

Example 1

According to the Invention

| Aqueous phase: | |
|---|---|
| Hostacerin AMPS (sold by the company Hoechst) | 2% |
| Preserving agents | 0.4% |
| Dye | 0.8% |
| Demineralized water | qs 100% |
| Oily phase: | |
| Cyclopentasiloxane | 6% |
| KSG 16 (containing 24% active material) (i.e. 1.2% active material) | 5% |
| 5-n-octanoylsalicylic acid | 0.01% |

Procedure: The water, the preserving agents and the dyes are heated at 75/80° C. The AMPS is dispersed therein with stirring until a smooth, transparent gel is obtained. The mixture is cooled to 55° C., followed by addition with stirring of the cyclopentasiloxane and the 5-n-octanoylsalicylic acid. The mixture is cooled to about 40° C. and the KSG-16 is added with stirring, followed by cooling to room temperature.

A smooth cream that is very gentle on the skin is obtained. Under a microscope, the KSG globules are well dispersed and the cream is uniform. This cream is capable of improving the radiance of the complexion of the skin while at the same time being very gentle.

Comparative Example 1

A composition identical to that of Example 1 but not containing any 5-n-octanoylsalicylic acid is prepared. The emulsion obtained is not particularly smooth, and shows under a microscope large globules of KSG.

Example 2

According to the Invention

| | |
|---|---|
| Aqueous phase: | |
| Hostacerin AMPS (sold by the company Hoechst) | 2% |
| Preserving agents | 0.4% |
| Dye | 0.8% |
| Demineralized water | qs 100% |
| Oily phase: | |
| Cyclopentasiloxane | 6% |
| KSG 16 (containing 24% active material) (i.e. 3.6% active material | 15% |
| 5-n-octanoylsalicylic acid | 0.01% |

The procedure is similar to that of Example 1.

A smooth cream that is very gentle on the skin is obtained. Under a microscope, the KSG globules are quite well dispersed and the cream is uniform. This cream is capable of improving the radiance of the complexion of the skin while at the same time being very gentle.

Comparative Example 2

A composition identical to that of Example 2 but not containing any 5-n-octanoylsalicylic acid is prepared. A granular emulsion is obtained, which shows under a microscope large plaques of KSG and KSG deposits on the edges of the emulsion.

Example 3

According to the Invention

| | |
|---|---|
| Aqueous phase: | |
| Hostacerin AMPS (sold by the company Hoechst) | 2% |
| Preserving agents | 0.4% |
| Dye | 0.8% |
| Demineralized water | qs 100% |
| Oily phase: | |
| Cyclopentasiloxane | 6% |
| KSG 16 (containing 24% active material) (i.e. 1.2% active material) | 5% |
| Undecylenoylglycine | 0.1% |

The procedure is similar to that of Example 1.

A smooth cream that is very gentle on the skin is obtained. Under a microscope, the KSG globules are well dispersed and the cream is uniform. This cream is capable of improving the radiance of the complexion of the skin while at the same time being very gentle.

Comparative Example 3

A composition identical to that of Example 3 but not containing any undecylenoylglycine is prepared. The emulsion obtained is not particularly smooth and shows under a microscope large globules of KSG.

Example 4

According to the Invention

| | |
|---|---|
| Aqueous phase: | |
| Hostacerin AMPS (sold by the company Hoechst) | 2% |
| Preserving agents | 0.4% |
| Dye | 0.8% |
| Demineralized water | qs 100% |
| Oily phase: | |
| Cyclopentasiloxane | 6% |
| KSG 16 (containing 24% active material) (i.e. 3.6% active material) | 15% |
| Undecylenoylglycine | 0.1% |

The procedure is similar to that of Example 1.

A smooth cream that is very gentle on the skin is obtained. Under a microscope, the KSG globules are quite well dispersed and the cream is uniform. This cream is capable of improving the radiance of the complexion of the skin while at the same time being very gentle.

Comparative Example 4

A composition identical to that of Example 4 but not containing any undecylenoylglycine is prepared. A granular emulsion is obtained, which shows under a microscope large plaques of KSG and KSG deposits on the edges of the emulsion.

Example 5

According to the Invention

| | |
|---|---|
| Aqueous phase: | |
| Hostacerin AMPS (sold by the company Hoechst) | 2% |
| Preserving agents | 0.4% |
| Dye | 0.8% |
| Demineralized water | qs 100% |
| Oily phase: | |
| Cyclopentasiloxane | 6% |
| KSG 16 (containing 24% active material) (i.e. 1.2% active material) | 5% |
| Sepicontrol (mixture containing 25% octanoylglycine) | 1% |

The procedure is similar to that of Example 1.

A smooth cream that is very gentle on the skin is obtained. Under a microscope, the KSG globules are well dispersed and the cream is uniform. This cream is capable of improving the radiance of the complexion of the skin while at the same time being very gentle.

Comparative Example 5

A composition identical to that of Example 5 but not containing any octanoylglycine is prepared. The emulsion obtained is not particularly smooth and shows under a microscope large globules of KGS.

Example 6

According to the Invention

| Aqueous phase: | |
|---|---|
| Hostacerin AMPS (sold by the company Hoechst) | 2% |
| Preserving agents | 0.4% |
| Dye | 0.8% |
| Demineralized water | qs 100% |
| Oily phase: | |
| Cyclopentasiloxane | 6% |
| KSG 16 (containing 24% active material) (i.e. 3.6% active material) | 15% |
| Sepicontrol (mixture containing 25% octanoylglycine) | 1% |

The procedure is similar to that of Example 1.

A smooth cream that is very gentle on the skin is obtained. Under a microscope, the KSG globules are quite well dispersed and the cream is uniform. This cream is capable of improving the radiance of the complexion of the skin while at the same time being very gentle.

Comparitive Example 6

A composition identical to that of Example 6 but not containing any octanoylglycine is prepared. A granular emulsion is obtained, which shows under a microscope large plaques of KSG and KSG deposits on the edges of the emulsion.

The above written description of the invention provides a manner and process of making and using it such that any person skilled in this art is enabled to make and use the same, this enablement being provided in particular for the subject matter of the appended claims, which make up a part of the original description and including a composition useful, for example, for topical application in the form of an oil-in-water emulsion comprising an oily phase dispersed in an aqueous phase, and a hydrophilic polymer, where the composition contains (1) at least one elastomeric organopolysiloxane and (2) at least one lipophilic derivative (compound) chosen from lipophilic amino acid derivatives (compounds) and lipophilic salicylic acid derivatives (compounds) of formula (I) below or a salt of such a compound:

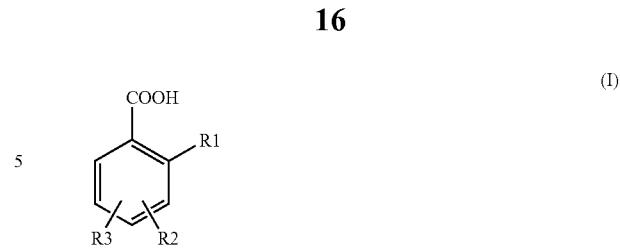

in which:

$R_1$ represents a hydroxyl radical or an ester of formula:

—O—CO—$R_4$ in which $R_4$ is a saturated or unsaturated aliphatic radical containing from 1 to 26 carbon atoms, an amine or thiol function optionally substituted with an alkyl radical containing from 1 to 18 carbon atoms, $R_2$ and $R_3$, independently of each other, are in position 3, 4, 5 or 6 on the benzene ring and represent, independently of each other, a hydrogen atom or a radical:

—(O)$_n$—(CO)$_m$—$R_5$ in which n and m, independently of each other, are each an integer equal to 0 or 1; on condition that $R_2$ and $R_3$ are not simultaneously hydrogen atoms;

$R_5$ represents a hydrogen, a linear, branched or cyclized saturated aliphatic radical containing from 1 to 18 carbon atoms, an unsaturated radical containing from 3 to 18 carbon atoms, bearing one to nine conjugated or non-conjugated double bonds, the radicals possibly being substituted with at least one substituent chosen from halogen atoms (fluorine, chlorine, bromine or iodine), trifluoromethyl radicals, hydroxyl in free form or esterified with an acid containing from 1 to 6 carbon atoms, or carboxyl in free form or esterified with a lower alcohol containing from 1 to 6 carbon atoms, or an aromatic radical containing from 6 to 10 carbon atoms.

Preferred embodiments of the invention similarly fully described and enabled include the use of a lipophilic derivative chosen from lipophilic salicylic acid derivatives of formula (I) and lipophilic amino acid derivatives, and salts thereof, to stabilize an oil-in-water emulsion containing an elastomeric organopolysiloxane and a hydrophilic polymer. Such stabilization may be accomplished by addition of the identified materials, where "addition" includes all orders of addition of materials eventually present in the final emulsion. Similarly enabled is the use of a composition according to the invention for treating, protecting, caring for, removing makeup from and/or cleansing the skin, the lips and/or the hair, and/or for making up the skin and/or the lips.

As used herein, the terms "derivative" and "compound" are interchangeable, and refer to materials of an identifiable chemical entity. One of ordinary skill in the art is able to identify a lipophilic amino acid compound, a salt thereof, a lipophilic salicylic acid compound, and a salt thereof.

All references, patents, applications, tests, standards, documents, publications, brochures, texts, articles, etc. mentioned herein are incorporated herein by reference. Where a numerical limit or range is stated, all values and subranges therewithin are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein.

What is claimed is:

1. A stable composition in the form of an oil-in-water emulsion comprising an oily phase dispersed in an aqueous phase and a hydrophilic polymer, said composition further comprising:
   (1) at least one elastomeric organopolysiloxane dispersed in the oily phase, wherein the elastomeric organopolysiloxane is present in an amount ranging from 1 to 20% by weight with respect to the total weight of the composition and is obtained by addition and crosslinking reaction, in the presence of a catalyst, of at least:
   a first organopolysiloxane (i) containing two vinyl groups in α-ω position on the silicone chain per molecule; and
   a second organopolysiloxane (ii) containing at least one hydrogen atom linked to a silicon atom per molecule, and
   (2) a glycine derivative selected from the group consisting of capryloylglycine, undecylenoylglycine, and mixtures thereof, wherein the glycine derivative is present in an amount sufficient to stabilize the composition, wherein the composition is free of surfactant.

2. The composition according to claim 1, wherein the amount of lipophilic compound(s) is 0.01% to 20% by weight relative to the total weight of the composition.

3. Composition according to claim 1, wherein the first organopolysiloxane (i) is an α,ω-dimethylvinylpolydimethylsiloxane.

4. The composition according to claim 1, wherein the organopolysiloxane is in a gel obtained according to the following steps:
   (a) mixing of first and second organopolysiloxanes (i) and (ii);
   (b) adding an oily phase to the mixture from step (a);
   (c) polymerizing the first and second organopolysiloxanes (i) and (ii) in the oily phase in the presence of a platinum catalyst.

5. The composition according to claim 1, wherein the amount of elastomeric organopolysiloxane(s) is 5% to 20% by weight relative to the total weight of the composition.

6. The composition according to claim 1, wherein the hydrophilic polymer is selected from the group consisting of carboxyvinyl polymers; acrylic or methacrylic copolymers; natural gums; polysaccharides; acrylamide polymers, and mixtures thereof.

7. The composition according to claim 1, wherein the hydrophilic polymer is a poly(meth)acrylamido($C_1$-$C_4$)alkylsulphonic acid.

8. The composition according to claim 7, wherein the poly(meth)acrylamido($C_1$-$C_4$)alkylsulphonic acid is crosslinked and at least 90% neutralized.

9. The composition according to claim 7, wherein the poly(meth)acrylamido($C_1$-$C_4$)alkylsulphonic acid is a polyacrylamidomethylpropane-sulphonic acid comprising, randomly distributed:
   a) from 90% to 99.9% by weight of units of formula (IV) below:

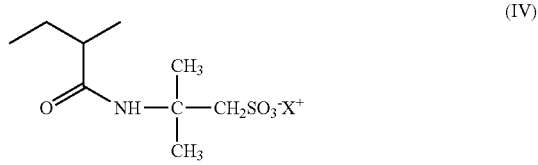

in which $X^+$ denotes a cation or a mixture of cations, including $H^+$,
   b) from 0.01% to 10% by weight of at least one crosslinking unit comprising at least two olefinic double bonds,
   the weight proportions of a) and b) being defined relative to the total weight of the polymer.

10. The composition according to claim 9, wherein the polyacrylamidomethylpropanesulphonic acid comprises from 98% to 99.5% by weight of units of formula (IV) and from 0.2% to 2% by weight of crosslinking units.

11. The composition according to claim 1, wherein the amount of hydrophilic polymer is 0.1% to 10% by weight relative to the total weight of the composition.

12. The composition according to claim 1, wherein the amount of oily phase is 1% to 50% by weight relative to the total weight of the composition.

13. The composition according to claim 1, wherein the oily phase comprises at least one volatile oil.

14. The composition according to claim 1, in the form of a cosmetic or dermatological composition.

15. A method for treating, protecting, caring for, removing makeup from and/or cleansing the skin, the lips and/or the hair, and/or for making up the skin and/or the lips, comprising applying the composition of claim 1 thereto.

16. The method of claim 15, wherein said method is a method for treating the skin, the hair and/or the lips comprising applying said composition to the skin, the hair and/or the lips.

17. The method of claim 15, wherein said method is a method for combating signs of ageing of the skin and/or to improve the radiance of the complexion of the skin.

* * * * *